(12) United States Patent
Klinder et al.

(10) Patent No.: US 11,064,955 B2
(45) Date of Patent: Jul. 20, 2021

(54) SHAPE SENSING ASSISTED MEDICAL PROCEDURE

(75) Inventors: Tobias Klinder, Uelzen (DE); Robert Manzke, Sleepy Hollow, NY (US); Raymond Chan, San Diego, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 594 days.

(21) Appl. No.: 14/008,187

(22) PCT Filed: Mar. 23, 2012

(86) PCT No.: PCT/IB2012/051396
§ 371 (c)(1),
(2), (4) Date: Sep. 27, 2013

(87) PCT Pub. No.: WO2012/131550
PCT Pub. Date: Oct. 4, 2012

(65) Prior Publication Data
US 2014/0039306 A1  Feb. 6, 2014

Related U.S. Application Data

(60) Provisional application No. 61/469,988, filed on Mar. 31, 2011.

(51) Int. Cl.
*A61B 5/06* (2006.01)
*A61B 34/20* (2016.01)
*A61B 6/03* (2006.01)
*G06T 19/00* (2011.01)
*A61B 1/267* (2006.01)

(52) U.S. Cl.
CPC .............. *A61B 6/032* (2013.01); *A61B 5/066* (2013.01); *G06T 19/003* (2013.01); *A61B 1/2676* (2013.01); *A61B 2034/2061* (2016.02)

(58) Field of Classification Search
CPC combination set(s) only.
See application file for complete search history.

(56) References Cited

U.S. PATENT DOCUMENTS

| | | | |
|---|---|---|---|
| 5,577,502 A | 11/1996 | Darrow et al. | |
| 5,638,819 A | 6/1997 | Manwaring et al. | |
| 6,346,940 B1 | 2/2002 | Fukunaga | |
| 6,580,938 B1 | 6/2003 | Acker | |
| 6,868,195 B2 | 3/2005 | Fujita | |
| 7,930,065 B2* | 4/2011 | Larkin | B25J 19/025 700/245 |
| 10,039,473 B2* | 8/2018 | Zhao | A61B 34/20 |

(Continued)

FOREIGN PATENT DOCUMENTS

| JP | 2002306403 A | 10/2002 |
|---|---|---|
| JP | 2002345725 A | 12/2002 |

(Continued)

*Primary Examiner* — Angela M Hoffa

(57) ABSTRACT

A system and method for shape sensing assistance in a medical procedure includes providing (402) a three-dimensional image of a distributed pathway system. A shape sensing enabled elongated device is introduced (406) into the pathway system. A shape of the elongated device in the pathway system is measured (410). The shape is compared (414) with the three-dimensional image to determine whether a given path has been selected relative to a target.

20 Claims, 3 Drawing Sheets

(56) References Cited

U.S. PATENT DOCUMENTS

| | | | |
|---|---|---|---|
| 10,085,671 B2* | 10/2018 | Duindam | A61B 5/0044 |
| 10,278,615 B2* | 5/2019 | Zhao | A61B 34/20 |
| 10,575,907 B2* | 3/2020 | Dekel | A61B 1/0005 |
| 10,582,879 B2* | 3/2020 | Glossop | A61B 8/5261 |
| 2002/0025017 A1* | 2/2002 | Stergiopoulos et al. | 378/8 |
| 2005/0182319 A1* | 8/2005 | Glossop | A61B 5/20 600/424 |
| 2005/0251017 A1* | 11/2005 | Azar | 600/407 |
| 2008/0118135 A1* | 5/2008 | Averbuch | G06T 7/187 382/131 |
| 2008/0183073 A1* | 7/2008 | Higgins | G06T 19/003 600/425 |
| 2009/0137952 A1 | 5/2009 | Ramamurthy et al. | |
| 2009/0292166 A1 | 11/2009 | Ito et al. | |
| 2010/0249506 A1* | 9/2010 | Prisco | A61B 1/00059 600/117 |
| 2011/0319910 A1* | 12/2011 | Roelle | A61B 34/71 606/130 |
| 2012/0289777 A1* | 11/2012 | Chopra | A61B 5/02028 600/109 |
| 2014/0243660 A1* | 8/2014 | Klinder | A61B 34/20 600/424 |
| 2015/0265368 A1* | 9/2015 | Chopra | A61B 5/7425 600/424 |
| 2019/0008413 A1* | 1/2019 | Duindam | A61B 5/065 |

FOREIGN PATENT DOCUMENTS

| | | |
|---|---|---|
| JP | 2009056239 A | 3/2009 |
| WO | WO2008115375 | 9/2008 |
| WO | WO2010111090 | 9/2010 |

\* cited by examiner

SHAPE SENSING ASSISTED MEDICAL PROCEDURE

CROSS-REFERENCE TO PRIOR APPLICATIONS

This application is the U.S. National Phase application under 35 U.S.C. § 371 of International Application Serial No. PCT/IB2012/051396, filed on Mar. 23, 2012, which claims the benefit of U.S. Application Ser. No. 61/469,988, filed on Mar. 31, 2011. These applications are hereby incorporated by reference herein.

This disclosure relates to shape sensing assisted procedures and more particularly to a system and method for utilizing shape sensing data to navigate a complex biological or mechanical system.

Taking tissue samples during bronchoscopy is a difficult task and has a low rate of success. During an intervention, a bronchoscope is inserted in the airways so that a physician can navigate to a target. However, the topology of the airways is very complex and the physician can easily get lost while going further down the bronchial tree.

One bronchoscope issue is that the bronchoscope provides only local information. In current clinical practice, a computed tomography (CT) image is typically acquired prior to the intervention for diagnosis and target definition. On the basis of the CT, computer tools assist the work-flow, e.g., segmentation of desired structures, optimal path calculation to the target, etc. Furthermore, the CT provides more global information of the patient's anatomy that can be used during the intervention. To track the path and register the bronchoscopic image with its position, electromagnetic (EM) tracking is usually employed. However, as the patient breathes during the intervention, a misalignment between CT and a bronchoscopic image limits the use of the image rendering. Real time X-ray imaging may also be employed to follow the device.

In accordance with the present principles, a system and method for shape sensing assistance in a medical procedure includes providing a three-dimensional image of a distributed pathway system. A shape sensing enabled elongated device is introduced into the pathway system. A shape of the elongated device in the pathway system is measured. The shape is compared with the three-dimensional image to determine whether a given path has been selected relative to a target. One aim is to provide the physician with some information and feedback if a desired path was chosen.

A method, in accordance with the present principles, includes providing a three-dimensional image of a distributed pathway system; introducing a shape sensing enabled elongated device into the pathway system; measuring a shape of the elongated device in the pathway system; and comparing the shape with the three-dimensional image to determine whether a given path has been selected relative to a target.

A system includes a three-dimensional image of a distributed pathway system. A shape sensing enabled elongated device is provided for insertion into the pathway system to measure a shape of the elongated device in the pathway system. A pathway determination module is configured to compute paths in the three-dimensional image and compare the shape with the paths in the three-dimensional image to determine whether a given path has been selected relative to a target.

Another system includes a processor and a memory device coupled to the processor and configured to store a three-dimensional image of a distributed pathway system, and a pathway determination module configured to compute paths in the three-dimensional image. A shape sensing enabled elongated device is provided for insertion into the pathway system to measure a shape of the elongated device in the pathway system. The pathway determination module is configured to compare the shape with the paths in the three-dimensional image to determine whether a given path has been selected relative to a target.

These and other objects, features and advantages of the present disclosure will become apparent from the following detailed description of illustrative embodiments thereof, which is to be read in connection with the accompanying drawings.

This disclosure will present in detail the following description of preferred embodiments with reference to the following figures wherein.

Figure 1:
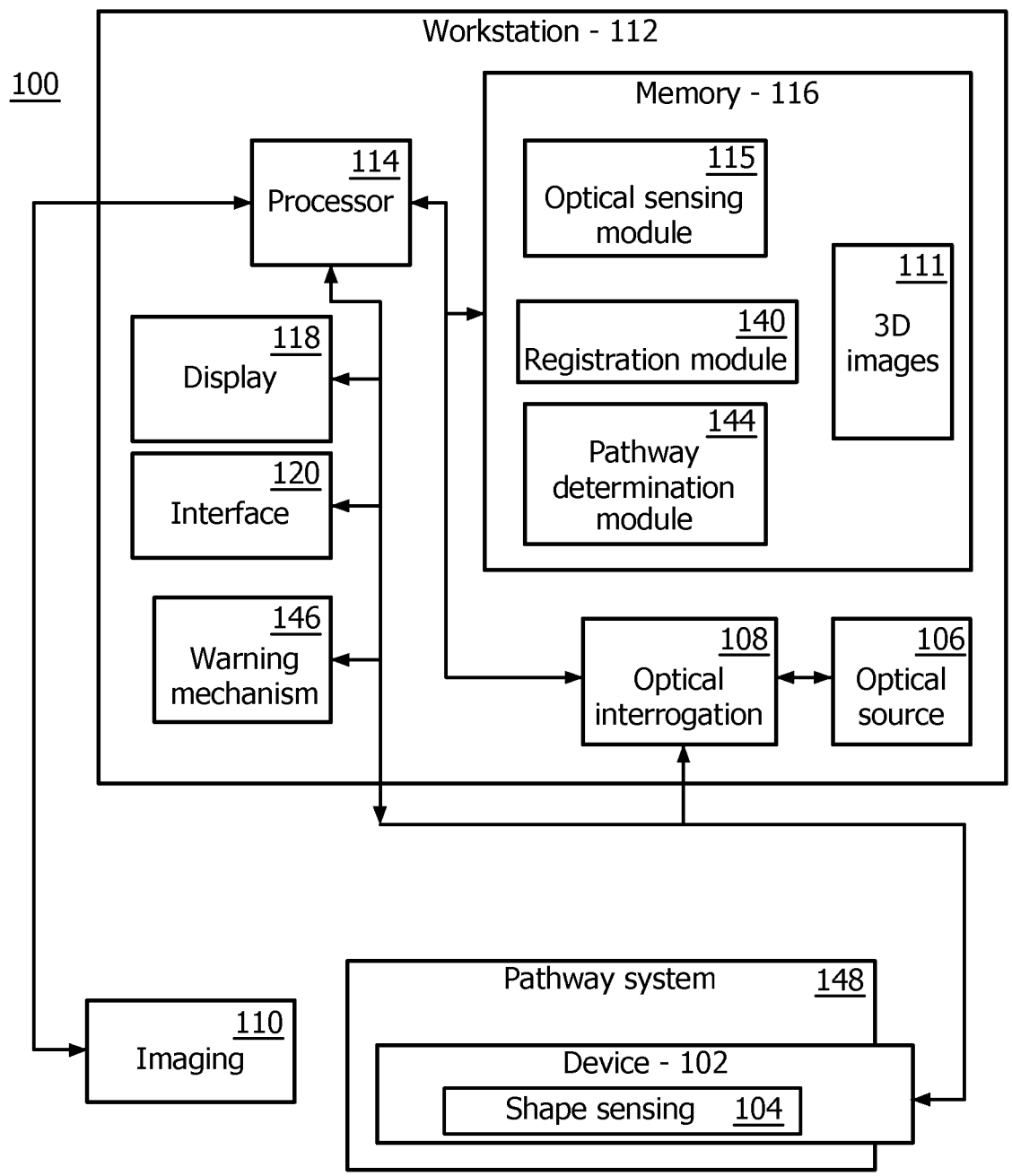
FIG. 1 is a block/flow diagram showing a system/method for shape sensing assistance in a medical procedure in accordance with the present principles.

In accordance with the present principles, device navigation is improved during a procedure by extracting shape-sensing data of a device. Tracking technology permits reconstruction of device shapes along a length of the device. The shape-sensed data and tracked position are then correlated with previously collected images. With shape sensing, three-dimensional (3D) information of the shape of the device (thus 3D information, e.g., compared to 2D information provided by X-ray or sparse 3D point information from electromagnetic tracking) is available. This shape information is of particular interest in complex systems, such as the airways in lungs, where the shape information can be employed to assist a physician to validate whether a correct path has been selected. Furthermore, sensors are attached to the device and can account for deformations caused by breathing or heart beat so that this motion can be compensated.

In one illustrative example, during a bronchoscopic procedure, a physician may attempt to reach a target with a bronchoscope that is inserted through the airways of the lungs. The topology of the airways is very complex which often causes physicians to navigate wrong paths. Even if pre-operative imaging data is available for guidance, deformations due to breathing or patient repositioning compromise successful targeting. The present principles employ shape sensing information obtained from the bronchoscope to reconstruct bronchoscope shapes along whole instrument lengths. This information can be used to overcome current limitations in bronchoscopic interventions by permitting a check between correct and incorrect device shapes which indicate correct or incorrect pathways to a target.

It should be understood that the present invention will be described in terms of medical instruments; however, the teachings of the present invention are much broader and are applicable to any instruments employed in tracking or analyzing complex biological or mechanical systems. In particular, the present principles are applicable to internal tracking procedures of biological systems, procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk—read only memory (CD-ROM), compact disk—read/write (CD-R/W) and DVD.

Referring now to the drawings in which like numerals represent the same or similar elements and initially to FIG. 1, a system 100 for performing a medical procedure is illustratively depicted. System 100 may include a workstation or console 112 from which a procedure is supervised and managed. Workstation 112 preferably includes one or more processors 114 and memory 116 for storing programs and applications. Memory 116 may store an optical sensing module 115 configured to interpret optical feedback signals from a shape sensing device 104. Optical sensing module 115 is configured to use the optical signal feedback (and any other feedback, e.g., electromagnetic (EM)) to reconstruct deformations, deflections and other changes associated with a medical device 102 and/or its surrounding region. The medical device 102 may include, e.g., a catheter, a guide wire, an endoscope, a probe, a robot, an electrode, a filter device, a balloon device, or other medical component, etc. Workstation 112 may include a display 118 for viewing internal images of a subject if an imaging system 110 is employed. The imaging system 110 may include, e.g., a magnetic resonance imaging (MRI) system, a fluoroscopy system, a computed tomography (CT) system, etc. Display 118 may also permit a user to interact with the workstation 112 and its components and functions. This is further facilitated by an interface 120 which may include a keyboard, mouse, a joystick or any other peripheral or control to permit user interaction with the workstation 112.

Workstation 112 includes an optical source 106 to provide optical fibers with light. An optical interrogation unit 108 is employed to detect light returning from all fibers. This permits the determination of strains or other parameters, which will be used to interpret the shape, orientation, etc. of the interventional device 102. The light signals will be employed as feedback to make adjustments to access errors and to calibrate the device 102 or system 100.

Shape sensing device 104 includes one or more fibers which are configured to exploit their geometry for detection and correction/calibration of a shape of the device 102. Optical interrogation unit/module 108 works with optical sensing module 115 (e.g., shape determination program) to permit tracking of instrument or device 102.

Imaging system 110 may be provided for collecting pre-operative imaging data or real-time intra-operative imaging data. The pre-operative imaging may be performed at another facility, location, etc. in advance of any procedure. These 3D images 111 may be stored in memory 116.

In a particularly useful embodiment, device 102 is employed to discover or observe a target. The target may include a lesion, injury site, object or other target. During the procedure, shape sensing data from shape sensing device 104 is collected and registered with the pre-operative imaging data. A registration module 140 determines registration positions and registers the shape sensing data with the pre-operative images 111, which are preferably 3D images. The shape sensing data may include motion data from a heartbeat and/or breathing and motion compensation may be performed to account for the same in the images (e.g., deformations due to breathing can be measured using shape sensing). The 3D images 111 may include these motion compensated images.

A pathway determination module 144 computes paths and compares rich point data from shape sensing data registered with the motion compensated images to determine whether a correct path was followed. The position and the shape of the device 102 is compared with the motion compensated images by matched pathways, e.g., in the lungs, with the shape of the device 102. If lumen walls appearing in the compensated image overlap the shape sensing data positions then a wrong pathway has been taken.

When a wrong path has been taken, the system 100 provides feedback to the clinician or physician. The feedback may take a plurality of different forms. For example, a visualization may be provided on display 118 which provides feedback to the physician that a wrong path was traveled and where the mistake most probably occurred to take corrective measures. Another embodiment provides an audible alarm when an incorrect path has been taken.

System 100 may include a warning mechanism 146 configured to indicate that an incorrect path has been selected. The warning mechanism 146 may take many forms and may be included in components that are already a part of the system 100. The warning mechanism 148 may include one or more of the following features. The display 118 may be employed to display a location where the incorrect path was selected so that a physician can go back and make corrections. In addition or alternatively, a visual (display 118) or audible (e.g., a speaker at interface 120) indicator may be generated when an incorrect path is selected. The warning mechanism 146 may be employed to warn of an imminent incorrect selection to effectively guide the physician during a procedure.

In one useful embodiment, the device 102 includes a bronchoscope, a pathway system 148 being analyzed includes a lung and the shape sensing includes optical shape sensing. The pre-operative images are obtained by computed tomography (CT) although other imaging methods may be employed. A global structure of airways of the lungs is extracted from the pre-operative images, and a path that is supposed to be chosen to reach a target is computed by pathway determination module 144. This path provides information about which path is supposed to be taken by the physician—thus limiting the possibilities where the bronchoscope can be.

Figure 2:
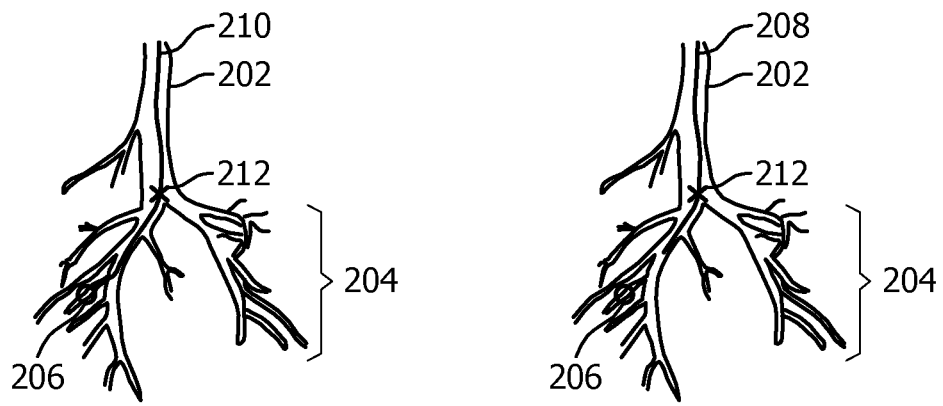
FIG. 2 is a diagram showing a centerline generated in a bifurcated image and for a shape sensed device for comparison in determining if a correct path has been taken in accordance with one embodiment.

Referring to FIG. 2, in one embodiment, the result of the shape sensing data and the compensated imaging data may generate centerlines to provide points of comparison. FIG. 2 depicts a bronchial tree 202 to be navigated during a procedure. The tree 202 includes many airways 204 that need to be navigated to reach a target 206. By the present principles, two centerlines are made available. One centerline 208 has its path measured by the shape sensing component while another centerline 210 is computed from a pre-operative image, such as a CT image, an MRI image, a fluoroscopy image, etc. These two centerlines 208 and 210 can now be compared. Based on the measured and the expected shape, a path selected by a physician can be verified. This path is modeled by the centerline 208 generated by the shape sensing data.

Characteristic points can be extracted (e.g., points at locations with very high curvature that belong to bifurcations). These points provide reference points to permit better verification as the patient breathes during the intervention. Based on these reference points, information is provided to the physician as to which direction to select at a next branching or bifurcation point. For example, a tip of the bronchoscope or other instrument is tracked to provide its current location so that a virtual rendering can be adapted and assist in decision making for which direction to take at a next decision point (e.g., a trachea bifurcation 212). For example, it can be extracted that the tip of the bronchoscope is 3 mm after the trachea. Thus, the virtual image can be adapted with respect to that information.

Having the two centerlines 208 and 210 permits motion compensation for local warping between an extracted airway tree and a measured shape. This can be employed to again adapt the virtual rendering or compensate motion locally. Local motion or warping may be as a result of physical changes such as blood flow, heart beat, breathing, etc., or from other sources, e.g., fusing images from two or more different sources, such as CT/X-Ray fusion, or local warping due to instrument presence. Local warping can also help to verify if the right path has been chosen. For example, bronchial segmentation (and thus the calculated path) can be locally warped according to a deformation field obtained from shape sensing measured centerlines (e.g., before and after deformation). Afterwards, a path can be verified to determine whether the computed path and the measured path match.

Figure 3:
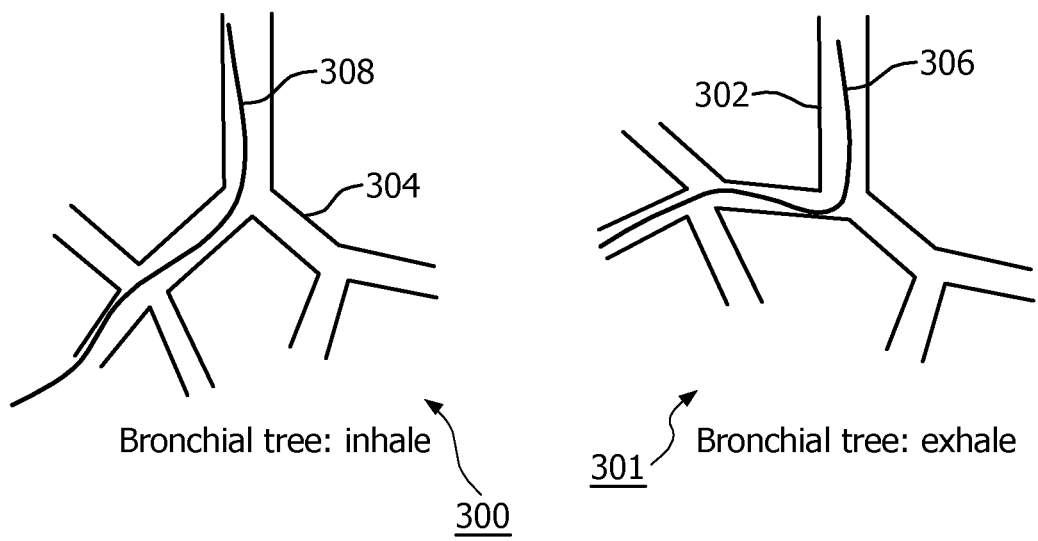
FIG. 3 is a diagram showing centerlines generated in bifurcated images and shape sensed measurement for a deforming organ for comparison in determining if a correct path has been taken in accordance with another embodiment.

Referring to FIG. 3, bronchial tree systems 300 and 301 are illustratively depicted, respectively for an inhale state and an exhale state. A measured path 306 for the exhale is overlaid on a bronchial tree image 302, and a measured path 308 for the inhale is overlaid on a bronchial tree image 304. From the two measurements 306 and 308, deformation can be computed. Registration of the measure paths 306 and 308 with each of the images 302 and 304 indicates whether the desired path was navigated since the data can be verified multiple times.

It should be understood that local motion compensation is usually sufficient, as the main interest is usually on an area around the calculated path where the target is located. Thus, e.g., local motion compensation is sufficient in a left main bronchus, while a right main bronchus is not of interest.

Figure 4:
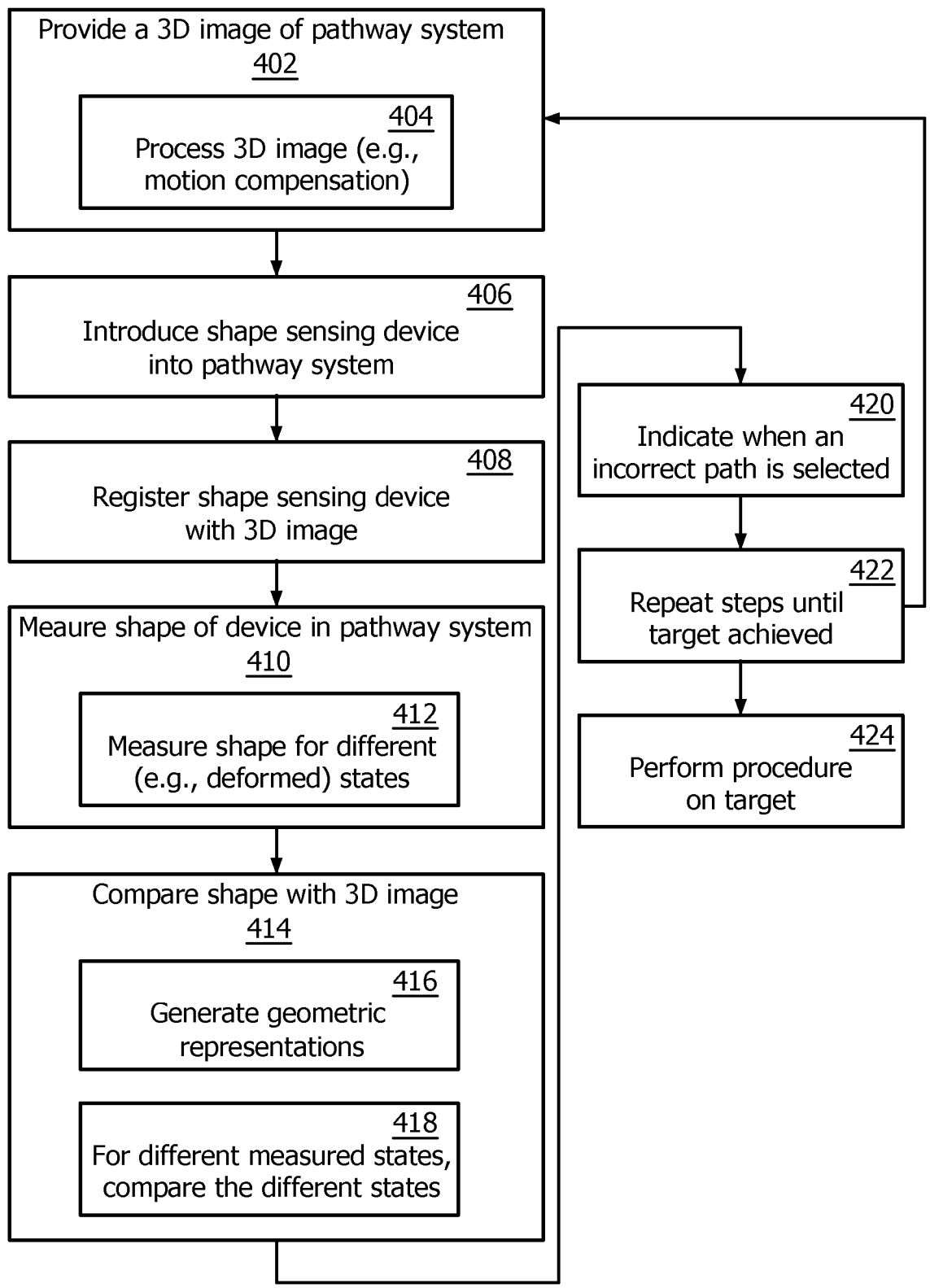
FIG. 4 is a block/flow diagram showing a method for shape sensing assistance in a medical procedure in accordance with the present principles.

Referring to FIG. 4, a method for shape sensing assistance in a medical procedure is illustratively shown in accordance with one embodiment. In block 402, a three-dimensional (3D) image of a distributed pathway system is provided. The 3D images may be created by segmenting CT images or images gathered through other systems or technologies (e.g., MRI, X-ray, etc.). The images may be processed for motion compensation or other corrections in block 404. The motion compensation may employ information from shape sensing.

In block 406, a shape sensing enabled elongated device is introduced into the pathway system. The pathway system may include a lung, a blood vessel, the heart, etc. The elongated device may include a catheter, guide wire, bronchoscope, etc. The shape sensing is preferably performed using an optical fiber shape sensing system although other shape sensing devices may be employed.

In block 408, the elongated device is preferably registered with the three-dimensional image. This may be performed using a tracking system (e.g., EM), physical guide posts or other registration methods. In block 410, a shape of the elongated device is measured in the pathway system. The measuring of the shape may include measuring a first shape of the elongated device in a first state and a second shape of the elongated device in a deformed state in block 412. By measuring the shape in different states (e.g., inhale/exhale, etc.), additional data is collected to increase the level of confidence in evaluating the correct pathways being navigated.

In block 414, the shape with the three-dimensional image is compared to determine whether a given path has been selected relative to a target. The target may include a lesion or other object of the procedure. In block 416, the comparison may include first generating geometric representations of the shape(s) and the three-dimensional images. In this way, the geometric representations may be compared. The geometric representations may include, e.g., centerlines, boundary lines, points of interest, etc. In block 418, when measuring the shapes in different states, a comparison between first and second shapes (e.g., inhale/exhale) to corresponding three-dimensional images may be performed to determine whether a correct path has been selected relative to the target.

In block 420, when an incorrect path has been selected, an indication of such may be made to the physician. The indication may include a warning of an imminent incorrect selection, a display of a location where the incorrect path was selected, and/or a visual or audible indication that the incorrect path was selected. In block 422, the process is repeated if necessary for each new decision. In block 424, the procedure is carried out with respect to the target.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function; and e) no specific sequence of acts is intended to be required unless specifically indicated.

Having described preferred embodiments for systems and methods for shape sensing assisted medical procedures (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A method, comprising:
providing a first three-dimensional image of a distributed pathway system of a biological body and having a plurality of paths in a first state;
determining a planned path of the plurality of paths in the first three-dimensional image;
introducing a shape sensing enabled elongated device into the distributed pathway system;
providing a second three-dimensional image of the distributed pathway system in a deformed state;
determining the planned path of the plurality of paths in the second three-dimensional image;
measuring a first three-dimensional shape of the elongated device in the distributed pathway system in the first state using shape sensing and measuring a second three-dimensional shape of the elongated device in the distributed pathway system in the deformed state;
registering at least one of the measured first three-dimensional shape of the elongated device with the first three-dimensional image or the measured second three-dimensional shape of the elongated device with the second three-dimensional image; and
comparing the measured first three-dimensional shape of the elongated device in the first state with a shape of the planned path in the first three-dimensional image, comparing the measured second three-dimensional shape of the elongated device in the deformed state with the shape of the planned path in the second three-dimensional image, and determining whether the elongated device has followed the planned path based on comparing the measured first three-dimensional shape of the elongated device in the first state with the shape of the planned path in the first three-dimensional image and comparing the measured second three-dimensional shape of the elongated device in the deformed state with the shape of the planned path in the second three-dimensional image, wherein deformation in the deformed state is determined based on sensors attached to the elongated device when in the distributed pathway.

2. The method as recited in claim 1, wherein comparing includes generating a first geometric representation of the measured first three-dimensional shape of the elongated device and a second geometric representation of the shape of the planned path in the first three-dimensional image and comparing the first geometric representation with the second geometric representation.

3. The method as recited in claim 2, wherein the first geometric representation and the second geometric representation include centerlines.

4. The method as recited in claim 1, further comprising indicating when the measured first three-dimensional shape of the elongated device does not match the shape of the planned path.

5. The method as recited in claim 1, wherein providing the second three-dimensional image includes providing a motion-compensated three-dimensional image.

6. The method of claim 1,
wherein the first three-dimensional shape of the elongated device in the first state is compared to the shape of the planned path in the first three-dimensional image at multiple positions, and
the second three-dimensional shape of the elongated device in the deformed state is compared to the shape of the planned path in the second three-dimensional image at multiple positions.

7. The method of claim 1, further comprising:
generating and displaying a virtual rendering that includes the second three-dimensional image and the measured second three-dimensional shape of the elongated device in the deformed state.

8. The method of claim 1, further comprising:
applying motion compensation to the first three-dimensional image to obtain the second three-dimensional image, wherein the motion compensation is based on measuring the second three-dimensional shape of the elongated device in the deformed state.

9. A system, comprising:
a memory device that stores executable software instructions, a first three-dimensional image of a distributed pathway system having a plurality of paths in a first state, and a second three-dimensional image of the distributed pathway system in a deformed state;
an elongated device for insertion into the distributed pathway system of a biological body, the elongated device having shape sensing for measuring a first three-dimensional shape of the elongated device in the distributed pathway system in the first state and for measuring a second three-dimensional shape of the elongated device in the distributed pathway system in the deformed state; and
a processor that executes the executable software instructions causing the processor to: register at least one of the measured first three-dimensional shape of the elongated device with the first three-dimensional image or the measured second three-dimensional shape of the elongated device with the second three-dimensional image; to determine a planned path of the plurality of paths in the first three-dimensional image; to determine the planned path of the plurality of paths in the second three-dimensional image; to compare the measured first three-dimensional shape of the elongated device in the first state with a shape of the planned path in the first three-dimensional image; to compare the measured second three-dimensional shape of the elongated device in the deformed state with the shape of the planned path in the second three-dimensional image; and to determine whether the planned path has been followed by the elongated device when inserted into the distributed pathway system based on comparing the measured first three-dimensional shape of the elongated device in the first state with the shape of the planned path in the first three-dimensional image and comparing the measured second three-dimensional shape of the elongated device in the deformed state with the shape of the planned path in the second three-dimensional image, wherein deformation in the deformed state is determined based on sensors attached to the elongated device when in the distributed pathway.

10. The system as recited in claim 9, wherein the executable software instructions further cause the processor to generate a first geometric representation of the measured first three-dimensional shape of the elongated device and a second geometric representation of the shape of the planned path in the first three-dimensional image and compares the first geometric representation with the second geometric representation.

11. The system as recited in claim 10, wherein the first geometric representation and the second geometric representation include centerlines.

12. The system as recited in claim 9, further comprising a warning mechanism comprising a display, or a speaker, or both, and configured to indicate when the measured first three-dimensional shape of the elongated device does not match the shape of the planned path.

13. The system as recited in claim 9, wherein the second three-dimensional image includes a motion-compensated three-dimensional image.

14. The system of claim 9,
wherein the first three-dimensional shape of the elongated device in the first state is compared to the shape of the planned path in the first three-dimensional image at multiple positions, and
the second three-dimensional shape of the elongated device in the deformed state is compared to the shape of the planned path in the second three-dimensional image at multiple positions.

15. The system of claim 9, wherein, when executed by the processor, the executable software instructions cause the system to:
generate and display a virtual rendering that includes the second three-dimensional image and the measured second three-dimensional shape of the elongated device in the deformed state.

16. The system of claim 9, wherein, when executed by the processor, the executable software instructions cause the system to:
apply motion compensation to the first three-dimensional image to obtain the second three-dimensional image, wherein the motion compensation is based on measuring the second three-dimensional shape of the elongated device in the deformed state.

17. A system, comprising:
a processor;
a memory device coupled to the processor and configured to store:
a first three-dimensional image of a distributed pathway system having a plurality of paths in a first state;
a second three-dimensional image of the distributed pathway system of a biological body in a deformed state;
executable software instructions that, when executed by the processor, are configured to register at least one of a measured first three-dimensional shape of an elongated device in the distributed pathway system with the first three-dimensional image or a measured second three-dimensional shape of the elongated device in the distributed pathway system with the second three-dimensional image; and executable software instructions that, when executed by the processor, cause the processor to determine a planned path of the plurality of paths in the first three-dimensional image and to determine the planned path of the plurality of paths in the second three-dimensional image;
wherein the elongated device for insertion into the distributed pathway system, the elongated device having shape sensing for measuring the first three-dimensional shape of the elongated device in the distributed pathway system in the first state and for measuring the second three-dimensional shape of the elongated device in the distributed pathway system in the deformed state,
wherein, when executed by the processor, the executable software instructions cause the processor to: compare the measured first three-dimensional shape of the elongated device in the first state with a shape of the planned path in the first three-dimensional image; to compare the measured second three-dimensional shape of the elongated device in the deformed state with the shape of the planned path in the second three-dimensional image; and to determine whether the planned path has been followed by the elongated device when inserted into the distributed pathway system based on comparing the measured first three-dimensional shape of the elongated device in the first state with the shape of the planned path in the first three-dimensional image and comparing the measured second three-dimensional shape of the elongated device in the deformed state with the shape of the planned path in the second three-dimensional image,
and wherein deformation in the deformed state is determined based on sensors attached to the elongated device when in the distributed pathway.

18. The system as recited in claim 17, wherein the executable software instructions further cause the processor to generate a first geometric representation of the measured first three-dimensional shape of the elongated device and a second geometric representation of the shape of the planned path in the first three-dimensional image and compare the first geometric representation with the second geometric representation.

19. The system of claim 17,
wherein the first three-dimensional shape of the elongated device in the first state is compared to the shape of the planned path in the first three-dimensional image at multiple positions, and
the second three-dimensional shape of the elongated device in the deformed state is compared to the shape of the planned path in the second three-dimensional image at multiple positions.

20. The system of claim 17, wherein, when executed by the processor, the executable software instructions cause the system to:

generate and display a virtual rendering that includes the second three-dimensional image and the measured second three-dimensional shape of the elongated device in the deformed state.

* * * * *